United States Patent
Xie

(10) Patent No.: US 11,866,493 B2
(45) Date of Patent: Jan. 9, 2024

(54) SINGLE-CHAIN VARIABLE FRAGMENT OF MET MONOCLONAL ANTIBODY AND METHODS OF USE IN CAR T CELL THERAPY

(71) Applicant: East Tennessee State University Research Foundation, Johnson City, TN (US)

(72) Inventor: Qian Xie, Johnson City, TN (US)

(73) Assignee: EAST TENNESSEE STATE UNIVERSITY RESEARCH FOUNDATION, Johnson City, TN (US)

( * ) Notice: Subject to any disclaimer, the term of this patent is extended or adjusted under 35 U.S.C. 154(b) by 218 days.

(21) Appl. No.: 17/086,839

(22) Filed: Nov. 2, 2020

(65) Prior Publication Data
US 2021/0130456 A1    May 6, 2021

Related U.S. Application Data

(60) Provisional application No. 62/929,285, filed on Nov. 1, 2019.

(51) Int. Cl.
| | |
|---|---|
| C07K 16/28 | (2006.01) |
| A61K 35/17 | (2015.01) |
| A61P 35/00 | (2006.01) |
| C07K 14/705 | (2006.01) |
| C07K 14/725 | (2006.01) |

(52) U.S. Cl.
CPC .............. *C07K 16/28* (2013.01); *A61K 35/17* (2013.01); *A61P 35/00* (2018.01); *C07K 14/7051* (2013.01); *C07K 14/70521* (2013.01); *C07K 14/70578* (2013.01); *C07K 2317/622* (2013.01); *C07K 2319/00* (2013.01)

(58) Field of Classification Search
CPC ................ C07K 16/28; C07K 14/7051; C07K 14/70521; C07K 14/70578; C07K 2317/622; C07K 2319/00; A61K 35/17; A61P 35/00
See application file for complete search history.

(56) References Cited

U.S. PATENT DOCUMENTS

| | | | |
|---|---|---|---|
| 10,040,846 B2 * | 8/2018 | Frigault | C12N 15/86 |
| 10,240,207 B2 * | 3/2019 | Yu | A61P 1/16 |
| 2011/0262436 A1 * | 10/2011 | Bender | A61K 39/39558 |
| | | | 424/138.1 |

FOREIGN PATENT DOCUMENTS

| | | | | |
|---|---|---|---|---|
| CN | 108707198 A | * | 10/2018 | C07K 14/7051 |
| CN | 110028584 A | * | 7/2019 | C07K 14/7051 |

OTHER PUBLICATIONS

Tchou, J., et al., "Safety and Efficacy of Intratumoral Injections of Chimeric Antigen Receptor (CAR) T Cells in Metastatic Breast Cancer," Cancer Immunology Research 5(12): 1152-1161 doi: 10.1158/2326-6066. (Epub Nov. 6, 2017) (Year: 2017).*
Wang (GenBank AAC18210, submitted Jul. 25, 2016; Wang, X. and Stollar, B, "Immunoglobulin VH gene expression in human aging," Clinical Immunology 93(2): 132-42 (1999). (Year: 2016).*
Guler-Gane, G., et al., "Overcoming the Refractory Expression of Secreted Recombinant Proteins in Mammalian Cells through Modification of the Signal Peptide and Adjacent Amino Acids," PLoS One 11(5): e0155340 doi: 10.1371/journal.pone.0155340. (May 19, 2016) (Year: 2016).*
Munoz-Lopez, P., et al., "Single-Chain Fragment Variable: Recent Progress in Cancer Diagnosis and Therapy," Cancers (Basel) 14 (17): 4206 doi: 10.3390/cancers14174206. (Aug. 30, 2022) (Year: 2022).*
Ochi, T., et al., "A single-chain antibody generation system yeilding CAR-T cells with superior antitumor function," Communications Biology 4(1): 273 doi: 10.1038/s42003-021-01791-1. (Mar. 2, 2021) (Year: 2021).*
Beatty, G., et al., "Mesothelin-specific chimeric antigen receptor mRNA-engineered T cells induce anti-tumor activity in solid malignancies," Cancer Immunology Research 2(2): 112-20 doi: 10.1158/2326-6066.CIR-13-0170. (Feb. 2014, published online Dec. 19, 2013) (Year: 2013).*
Srivastava, S. and Riddell, S., "Engineering CAR-T cells: Design concepts," Trends Immunoloy 36(8): 494-502 doi: 10.1016/j.it.2015.06.004. (Epub Jul. 11, 2015) (Year: 2015).*
Stoiber, S. et al., "Limitations in the Design of Chimeric Antigen Receptors for Cancer Therapy," Cells 8(5): 472 doi: 10.3390/cells8050472. (May 17, 2019) (Year: 2019).*
Merchant, et al., "Monovalent antibody design and mechanism of action of onartuzumab, a MET antagonist with anti-tumor activity as a therapeutic agent", PNAS, E2987-E2996, Jul. 23, 2013.

\* cited by examiner

*Primary Examiner* — Taeyoon Kim
*Assistant Examiner* — Eric J Rogers
(74) *Attorney, Agent, or Firm* — Dinsmore & Shohl LLP

(57) ABSTRACT

A single-chain variable fragment (ScFv) derived from anti-c-Met monoclonal antibody MetMAb that specifically binds to c-Met receptor is provided. Also provided are chimeric antigen receptor (CAR) vectors including the ScFv, human T cells transduced with the disclosed CAR vectors, pharmaceutical compositions including the CAR T cells, ScFv fusion proteins, and methods of treating a c-Met-positive cancer or a cancer characterized by overexpression of c-Met in a subject in need thereof by administering an effective amount of the disclosed CAR T cells.

13 Claims, 8 Drawing Sheets
Specification includes a Sequence Listing.

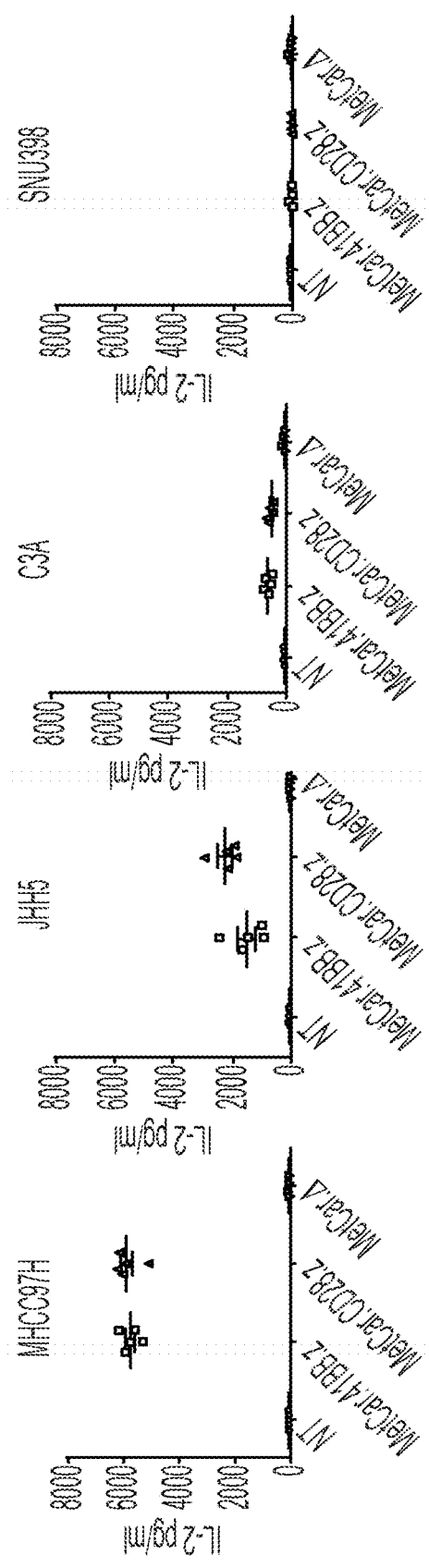
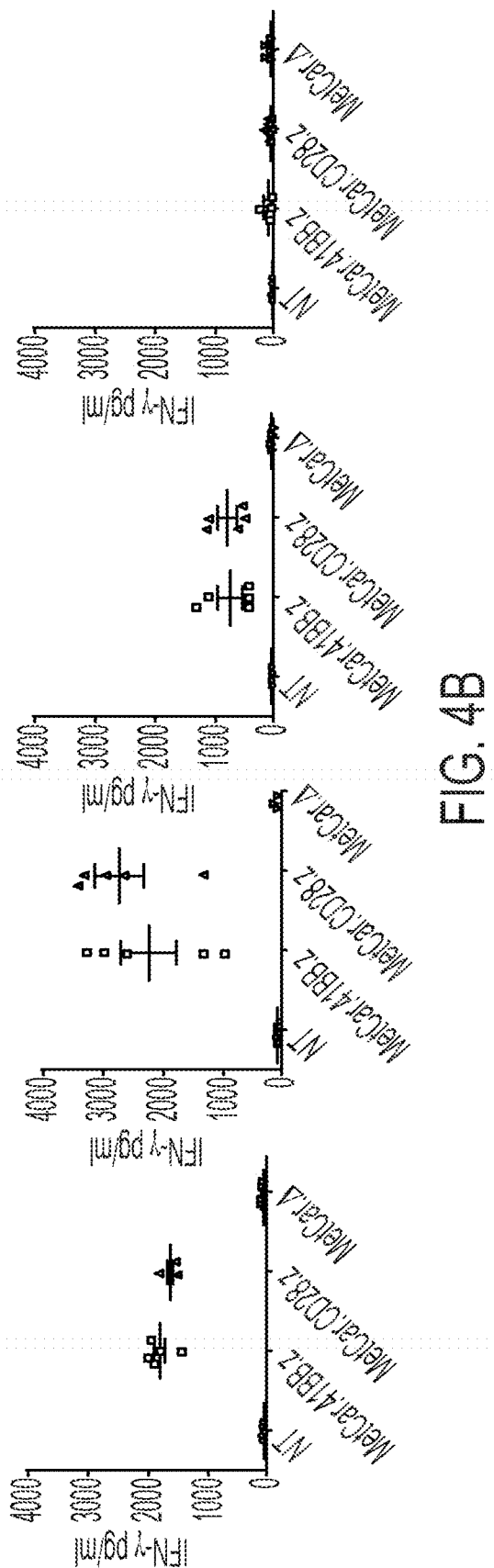
FIG. 4A
FIG. 4B

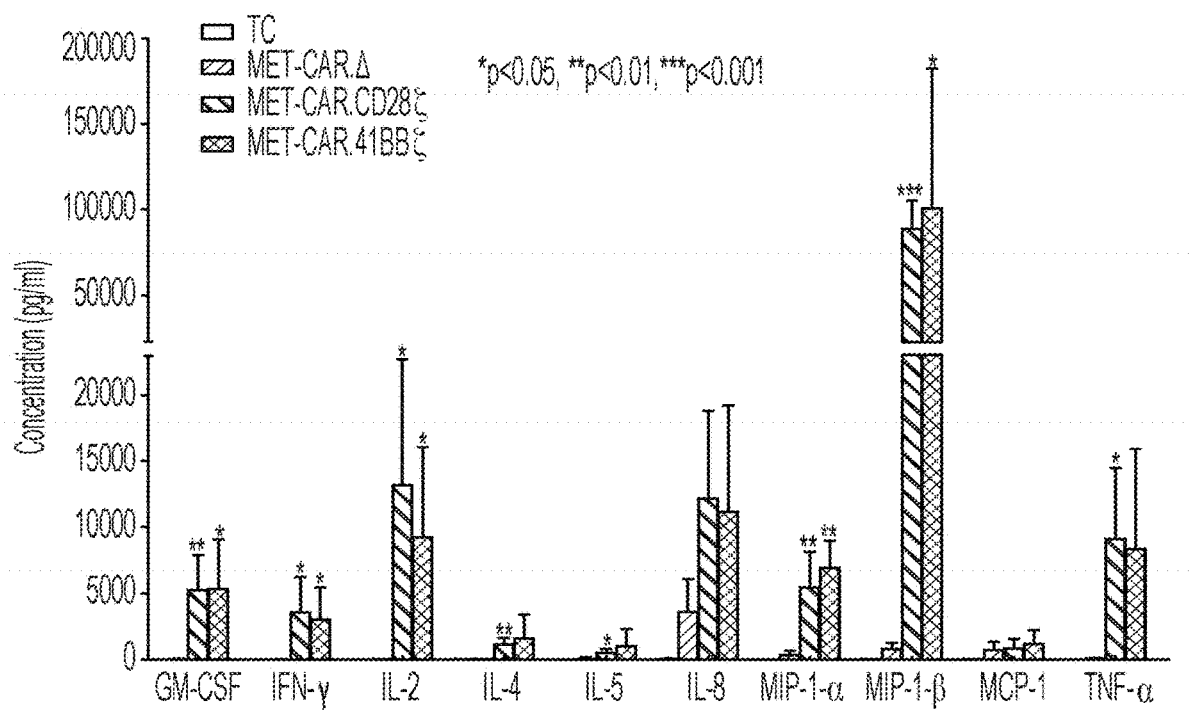
FIG. 5A
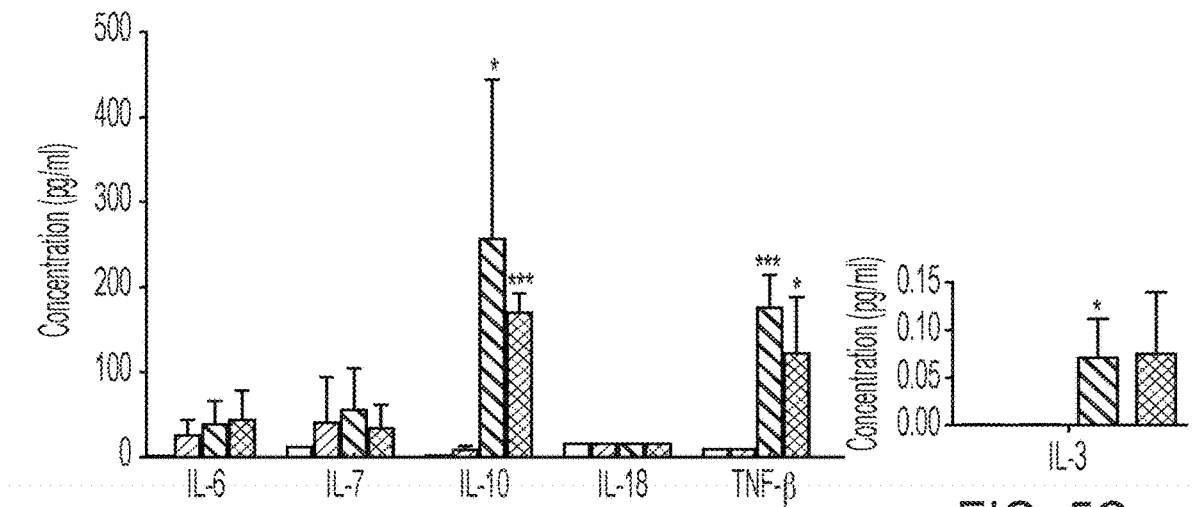
FIG. 5B
FIG. 5C

SEQUENCE LISTING

```
<160> NUMBER OF SEQ ID NOS: 9

<210> SEQ ID NO 1
<211> LENGTH: 797
<212> TYPE: DNA
<213> ORGANISM: Artificial Sequence
<220> FEATURE:
<223> OTHER INFORMATION: ScFv engineered construct
<220> FEATURE:
<221> NAME/KEY: misc_feature
<223> OTHER INFORMATION: A-T designed mutation to avoid internal Nco I
      site

<400> SEQUENCE: 1
attggatctg gcgcatcctg tttctcgtgg gagccgccac aggcgcccac tctgaggtgc      60
agctggtgga gtctggtggc ggcctggttc agccaggcgg tagcctgcgt ctgtcttgcg     120
cagccagcgg ctacaccttc accagctatt ggctgcactg ggtgcgccaa gcccaggca     180
```

```
agggtctgga gtgggtgggt atgattgacc ctagcaacag cgacacccgt tcaatccaa    240 acttcaaaga ccgctttacc attagcgccg acaccagcaa gaacaccgcc tatctgcaga   300
tgaactctct ccgcgccgag gacaccgccg tgtactactg cgccacctat cgcagctacg   360
ttacacctct ggactactgg ggccagggca cctggtgac cgtgagcagc ggaggcggag     420
gatcaggcgg cggaggaagt ggcggagggg gaagcgacat tcagatgaca cagtctccta   480
gctctctgtc tgcctctgtg gcgaccgtg ttaccattac ctgcaaaagc agccagagcc    540
tgctgtacac cagcagccag aagaactatc tggcatggta tcagcagaag ccaggcaaag   600
cacctaaact gctcatctac tgggccagca cccgcgaaag cggcgttcct tctcgcttta   660
gcggcagcgg tagcggtaca gacttcaccc tgaccatcag cagcctgcag cctgaggatt   720
tcgccaccta ttactgccag cagtactacg cctatccttg acattcggt cagggcacaa    780 aagtggagat caaggat                                                  797

<210> SEQ ID NO 2
<211> LENGTH: 53
<212> TYPE: DNA
<213> ORGANISM: Artificial Sequence
<220> FEATURE:
<223> OTHER INFORMATION: Signal peptide sequence

<400> SEQUENCE: 2
attggatctg gcgcatcctg tttctcgtgg gagccgccac aggcgcccac tct           53

<210> SEQ ID NO 3
<211> LENGTH: 45
<212> TYPE: DNA
<213> ORGANISM: Artificial Sequence
<220> FEATURE:
<223> OTHER INFORMATION: Linker sequence

<400> SEQUENCE: 3
ggaggcggag gatcaggcgg cggaggaagt ggcggagggg gaagc                    45

<210> SEQ ID NO 4
<211> LENGTH: 357
<212> TYPE: DNA
<213> ORGANISM: Artificial Sequence
<220> FEATURE:
<223> OTHER INFORMATION: VH domain of Met mAb

<400> SEQUENCE: 4
gaggtgcagc tggtggagtc tggtggcggc ctggttcagc caggcggtag cctgcgtctg    60
tcttgcgcag ccagcggcta caccttcacc agctattggc tgcactgggt gcgccaagcc   120
ccaggcaagg gtctggagtg ggtgggtatg attgaccta gcaacagcga cacccgtttc    180
aatccaaact tcaaagaccg ctttaccatt agcgccgaca ccagcaagaa caccgcctat   240
ctgcagatga actctctccg cgccgaggac accgccgtgt actactgcgc cacctatcgc   300
agctacgtta cacctctgga ctactggggc cagggcaccc tggtgaccgt gagcagc      357

<210> SEQ ID NO 5
<211> LENGTH: 342
<212> TYPE: DNA
<213> ORGANISM: Artificial Sequence
<220> FEATURE:
<223> OTHER INFORMATION: VL domain of Met mAb
<220> FEATURE:
<221> NAME/KEY: misc_feature
<222> LOCATION: (303)..(303)
```

<223> OTHER INFORMATION: Designed mutation of A-T to avoid internal
      Nco I site.

<400> SEQUENCE: 5

```
gacattcaga tgacacagtc tcctagctct ctgtctgcct ctgtgggcga ccgtgttacc      60
attacctgca aaagcagcca gagcctgctg tacaccagca gccagaagaa ctatctggca    120
tggtatcagc agaagccagg caaagcacct aaactgctca tctactgggc cagcacccgc    180
gaaagcggcg ttccttctcg ctttagcggc agcggtagcg gtacagactt cacccctgac    240
atcagcagcc tgcagcctga ggatttcgcc acctattact gccagcagta ctacgcctat    300
ccttggacat tcggtcaggg cacaaaagtg gagatcaagg at                       342
```

<210> SEQ ID NO 6
<211> LENGTH: 809
<212> TYPE: DNA
<213> ORGANISM: Artificial Sequence
<220> FEATURE:
<223> OTHER INFORMATION: ScFv construct including Nco I and Xho I sites

<400> SEQUENCE: 6

```
ccatggattg gatctggcgc atcctgtttc tcgtgggagc cgccacaggc gcccactctg      60
aggtgcagct ggtggagtct ggtggcggcc tggttcagcc aggcggtagc ctgcgtctgt    120
cttgcgcagc cagcggctac accttcacca gctattggct gcactgggtg cgccaagccc    180
caggcaaggg tctggagtgg gtgggtatga ttgaccctag caacagcgac accgtttca     240
atccaaactt caaagaccgc tttaccatta gcgccgacac cagcaagaac accgcctatc    300
tgcagatgaa ctctctccgc gccgaggaca ccgccgtgta ctactgcgcc acctatcgca    360
gctacgttac acctctggac tactggggcc agggcaccct ggtgaccgtg agcagcggag    420
gcggaggatc aggcggcgga ggaagtggcg gaggggaag cgacattcag atgacacagt    480
ctcctagctc tctgtctgcc tctgtgggcg accgtgttac cattacctgc aaaagcagcc    540
agagcctgct gtacaccagc agccagaaga actatctggc atggtatcag cagaagccag    600
gcaaagcacc taaactgctc atctactggg ccagcacccg cgaaagcggc gttccttctc    660
gctttagcgg cagcggtagc ggtacagact tcaccctgac catcagcagc ctgcagcctg    720
aggatttcgc cacctattac tgccagcagt actacgccta ccttggaca ttcggtcagg    780
gcacaaaagt ggagatcaag gatctcgag                                       809
```

<210> SEQ ID NO 7
<211> LENGTH: 269
<212> TYPE: PRT
<213> ORGANISM: Artificial Sequence
<220> FEATURE:
<223> OTHER INFORMATION: ScFv fusion peptide, including signal peptide
      and linker

<400> SEQUENCE: 7

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Thr Phe
        35                  40                  45

Thr Ser Tyr Trp Leu His Trp Val Arg Gln Ala Pro Gly Lys Gly Leu
    50                  55                  60

Glu Trp Val Gly Met Ile Asp Pro Ser Asn Ser Asp Thr Arg Phe Asn
```

```
                65                  70                  75                  80
Pro Asn Phe Lys Asp Arg Phe Thr Ile Ser Ala Asp Thr Ser Lys Asn
                    85                  90                  95

Thr Ala Tyr Leu Gln Met Asn Ser Leu Arg Ala Glu Asp Thr Ala Val
                100                 105                 110

Tyr Tyr Cys Ala Thr Tyr Arg Ser Tyr Val Thr Pro Leu Asp Tyr Trp
                115                 120                 125

Gly Gln Gly Thr Leu Val Thr Val Ser Gly Gly Gly Ser Gly
                130                 135                 140

Gly Gly Gly Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Lys Ser Ser Gln Ser Leu Leu Tyr Thr Ser Ser Gln Lys Asn Tyr Leu
                180                 185                 190

Ala Trp Tyr Gln Gln Lys Pro Gly Lys Ala Pro Lys Leu Leu Ile Tyr
                195                 200                 205

Trp Ala Ser Thr Arg Glu Ser Gly Val Pro Ser Arg Phe Ser Gly Ser
                210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Tyr Tyr Ala Tyr Pro Trp Thr
                245                 250                 255

Phe Gly Gln Gly Thr Lys Val Glu Ile Lys Asp Leu Glu
                260                 265

<210> SEQ ID NO 8
<211> LENGTH: 119
<212> TYPE: PRT
<213> ORGANISM: Artificial Sequence
<220> FEATURE:
<223> OTHER INFORMATION: VH domain amino acid sequence

<400> SEQUENCE: 8

Glu Val Gln Leu Val Glu Ser Gly Gly Gly Leu Val Gln Pro Gly Gly
1                   5                   10                  15

Ser Leu Arg Leu Ser Cys Ala Ala Ser Gly Tyr Thr Phe Thr Ser Tyr
                20                  25                  30

Trp Leu His Trp Val Arg Gln Ala Pro Gly Lys Gly Leu Glu Trp Val
                35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
                100                 105                 110

Thr Leu Val Thr Val Ser Ser
        115

<210> SEQ ID NO 9
<211> LENGTH: 114
<212> TYPE: PRT
<213> ORGANISM: Artificial Sequence
<220> FEATURE:
<223> OTHER INFORMATION: VL domain amino acid sequence
```

```
<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Asp
```

SINGLE-CHAIN VARIABLE FRAGMENT OF MET MONOCLONAL ANTIBODY AND METHODS OF USE IN CAR T CELL THERAPY

CROSS-REFERENCE TO RELATED APPLICATIONS

This application claims priority to U.S. Provisional Application Ser. No. 62/929,285, filed Nov. 1, 2019, the entire contents of which are incorporated herein by reference.

STATEMENT REGARDING FEDERALLY SPONSORED RESEARCH OR DEVELOPMENT

This invention was made with Government support under W81XWH-19-1-0811 awarded by the U.S. Department of Defense. The Government has certain rights in the invention.

TECHNICAL FIELD

This disclosure relates to the field of chimeric antigen receptor T cell (CAR T) therapy. Specifically, this disclosure relates to single chain variable fragments (ScFv) derived from anti-Met monoclonal antibody (MetMAb) and their methods of use in CAR T therapy.

SEQUENCE LISTING

Applicant incorporates by reference a CRF sequence listing submitted herewith having file name Sequence_Listing_37156_16.txt, created on Oct. 28, 2019.

The nucleic and amino acid sequences listed in the accompanying sequence listing are shown using standard abbreviations as defined in 37 C.F.R. 1.822. In the accompanying sequence listing:
  SEQ ID NO: 1 represents a nucleic acid sequence of an ScFv engineered construct;
  SEQ ID NO: 2 represents a nucleic acid sequence of a signal peptide;
  SEQ ID NO: 3 represents a nucleic acid sequence of a linker peptide;
  SEQ ID NO: 4 represents a nucleic acid sequence of a $V_H$ domain of an ScFv according to the disclosure;
  SEQ ID NO: 5 represents a nucleic acid sequence of a $V_L$ domain of an ScFv according to the disclosure;
  SEQ ID NO: 6 represents a nucleic acid sequence of an ScFv engineered construct, including NcoI and XhoI restriction sites;
  SEQ ID NO: 7 represents an amino acid sequence of an ScFv engineered fusion protein.
  SEQ ID NO: 8 represents an amino acid sequence of a VH domain of an ScFv according to the disclosure; and
  SEQ ID NO: 9 represents an amino acid sequence of a VL domain of an ScFv according to the disclosure.

BACKGROUND

Hepatocellular carcinoma (HCC) is the most common form of liver cancer and is a leading cause of cancer mortality world-wide. While hepatitis B virus (HBV)/hepatitis C virus (HCV) infection is the major cause of HCC, aberrant activation of c-Met oncogene (mesenchymal epithelial transition factor, also referred to as tyrosine-protein kinase Met or hepatocyte growth factor (HGF) receptor), plays a primary role in carcinogenesis and cancer progression. MET single gene overexpression occurs in approximately 40-50% of HCC patients and is correlated to a short survival time. MET-regulated multigene signatures indicate aggressive phenotype and poor prognosis. Experimentally, overproduction of the HBV L envelope protein alone formed HBV surface antigen (HBsAg) particles that accumulated at high concentration in hepatocytes and induced carcinogenesis. This process can be significantly enhanced by HGF stimulation, leading to HCC with more a malignant phenotype. As such, MET has been identified as an important target for treating advanced HCC.

In patients with advanced HCC, conventional chemotherapy is generally ineffective. While targeted therapeutics are more favored due to their specificity, the multi-kinase inhibitor sorafenib (Nexavar®) was the only FDA approved non-selective inhibitor for standard care of HCC, which provides limited survival benefit. Since MET has been recognized as a promising target, several small molecule inhibitors and antibodies have been developed and tested in clinical trials against advanced HCC. Cabozantinib, a non-selective ATP competitor targeting MET, VEGFR2, and AXL has shown promising clinical results to prolong median survival in advanced HCC patients with both sorafenib-pretreated and sorafenib-naïve patients under manageable toxicity, is now FDA approved for treatment of HCC patients who previously received sorafenib treatment, although long-term efficacy versus toxicity remains elusive. Tivantinib (ARQ197) is a selective non-ATP competitor that showed efficacy in a phase II trial against HCC. However, toxicity has been of concern, as certain efficacies are found independent of MET inhibition. Like other tyrosine kinase inhibitors (TKIs), emerging challenges for MET inhibitors include signaling pathway bypass and acquired resistance.

Given recent breakthroughs in cancer immunotherapy, genetically modified T cells with chimeric antigen receptors (CAR T cells) provide a promising approach for treating cancer. Targeting MET using CAR T cell therapy allows dual critical functions within a single reagent: specific MET-expressing tumor targeting, and T cell-mediated killing activity. Because MetCAR T cells function through T cell receptor (TCR) rather than the MET RTK signaling pathway, efficacy is less dependent upon MET signaling inhibition or bypass and is unrelated to pretreated therapeutics. As such, MetCAR T cells may target MET more effectively than small molecule inhibitors or antibodies. Most recently, an mRNA-based Met-targeting CAR T cell therapy has shown favorable results for treating metastatic breast cancer and is moving forward in clinical trials.

The efficacy of CAR T cell therapy depends on multiple factors, including the choice of target antigen and single-chain variable fragment (ScFv) domain. MetMAb, a validated anti-MET monoclonal antibody, potently inhibits HGF-dependent—but not MET-amplified—tumor growth. See US 2011/0262436, incorporated herein by reference in its entirety. Studies have demonstrated that MetMAb functions though blocking the HGF/MET binding domain at an extracellular level, rather than the intracellular MET kinase domain. While MetMAb failed in clinical phase III trials due to lack of efficacy, it remains a valuable and safe tumor targeting reagent due to the specificity and high affinity in binding to MET extracellular domain. Further, MetMAb demonstrated a lack of toxicity in clinical trials.

A need persists for improved therapeutics and methods of treating hepatocellular carcinoma.

SUMMARY

Accordingly, provided herein is a novel single-chain variable fragment (ScFv) sequence derived from MetMAb, a validated anti-MET monoclonal antibody, which has been further cloned into two second-generation CAR vectors. Results show that both MET-targeting CAR vectors have high efficacy in transducing healthy human T cells that specifically inhibit Met-positive HCC cells. The presently disclosed agents are advantageously useful for the treatment of malignant HCC and other types of cancer characterized by MET overexpression.

In one embodiment, a chimeric antigen receptor (CAR) vector comprising a single-chain variable fragment (ScFv) derived from MetMAb is provided, wherein the ScFv specifically binds to MET receptor.

In another embodiment, a human T cell transduced with a chimeric antigen receptor (CAR) vector comprising a single-chain variable fragment (ScFv) derived from MetMAb is provided, wherein the ScFv specifically binds to MET receptor.

In another embodiment, a method of treating a cancer characterized by overexpression of MET in a subject in need thereof is provided, the method comprising administering to the subject an effective amount of a human T cell transduced with a chimeric antigen receptor (CAR) vector comprising a single-chain variable fragment (ScFv) derived from MetMAb, wherein the ScFv specifically binds to MET receptor.

In another embodiment, a method of treating a MET-positive cancer in a subject in need thereof is provided, the method comprising administering to the subject an effective amount of human T cells transduced with a chimeric antigen receptor (CAR) vector comprising a single-chain variable fragment (ScFv) derived from MetMAb, wherein the ScFv specifically binds to MET receptor.

In another embodiment, a pharmaceutical composition is provided, comprising: a human T cell transduced with a chimeric antigen receptor (CAR) vector comprising a single-chain variable fragment (ScFv) derived from MetMAb, wherein the ScFv specifically binds to MET receptor; and a pharmaceutically-acceptable carrier.

These and other objects, features, embodiments, and advantages will become apparent to those of ordinary skill in the art from a reading of the following detailed description and the appended claims.

BRIEF DESCRIPTION OF THE DRAWINGS

The details of embodiments of the presently-disclosed subject matter are set forth in this document. Modifications to embodiments described in this document, and other embodiments, will be evident to those of ordinary skill in the art after a study of the information provided in this document.

FIG. 4A is a series of graphs showing IL-2 release by MetCAR T cells after co-culture with HCC cells in vitro. MHCC97H, C3A, JHH5, and SNU398 cells were seeded in 24-well plate for 24 hrs followed by adding MetCAR T cells at different E:T=2:1 ratio. After additional 24 hrs, media were collected for ELISA analysis for IL-2.

FIG. 4B is a series of graphs showing IFNγ release by MetCAR T cells after co-culture with HCC cells in vitro. MHCC97H, C3A, JHH5, and SNU398 cells were seeded in 24-well plate for 24 hrs followed by adding MetCAR T cells at different E:T=2:1 ratio. After additional 24 hrs, media were collected for ELISA analysis for IFNγ.

FIG. 5A is a graph showing multi-panel cytokine released (>500 pg/ml) after co-culture of MET-CAR T cells with MHCC97H.

FIG. 5B is a graph showing multi-panel cytokine released (0-500 pg/ml) after co-culture of MET-CAR T cells with MHCC97H.

FIG. 5C is a graph showing IL-3 release after co-culture of MET-CAR T cells with MHCC97H.

DETAILED DESCRIPTION

Figure 1A:
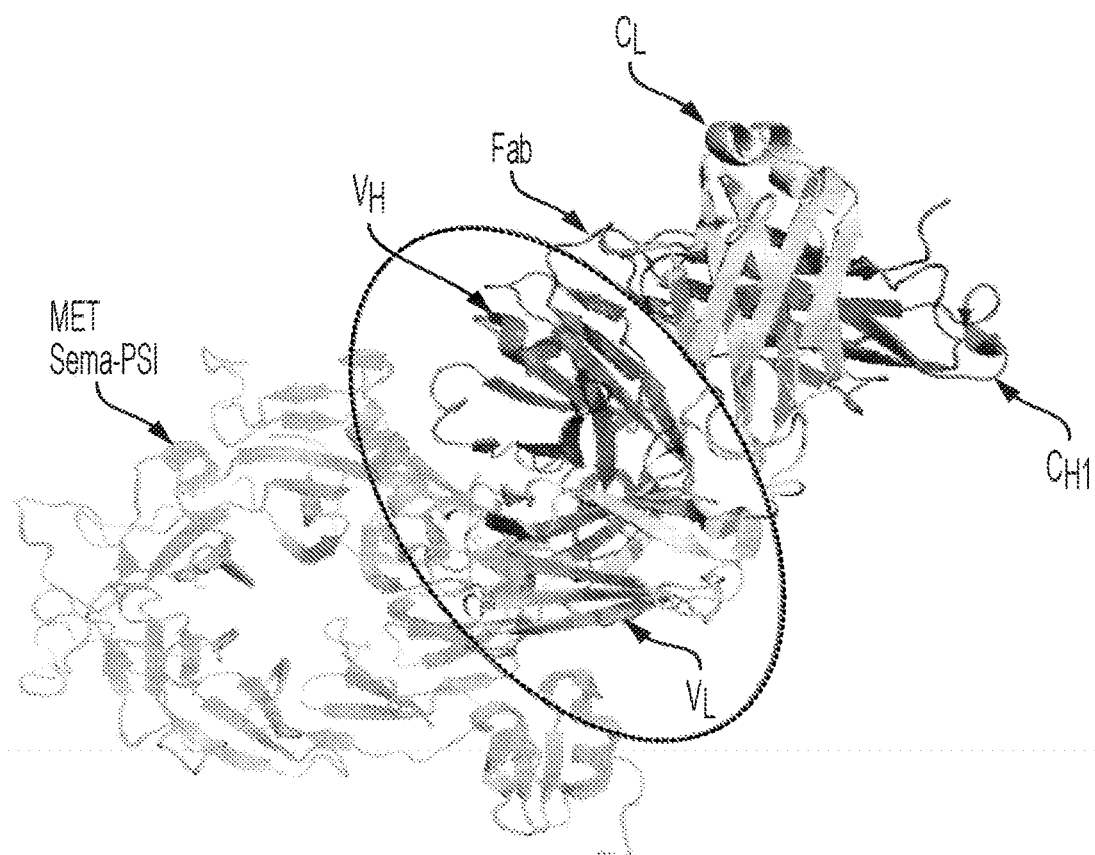
FIG. 1A is computational model of a crystal structure showing MetMAb Fab domain in binding to MET Sema-PSI domain (edited from PDB code 4K3J). $V_H$ and $V_L$ domains (circled) are the least required structures to form the binding.

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in this specification and the appended claims, the singular forms "a," "an" and "the" include plural references unless the content clearly dictates otherwise.

As used herein, a "subject" refers to a mammalian subject. Optionally, a subject is a human or non-human primate. Optionally, the subject is selected from the group consisting of mouse, rat, rabbit, monkey, pig, and human. In a specific embodiment, the subject is a human.

The terms "treat," "treatment," and "treating," as used herein, refer to a method of alleviating or abrogating a disease, disorder, and/or symptoms thereof in a subject.

"Specifically" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

Single-Chain Variable Fragment

Single-chain variable fragments (ScFvs) are fusion proteins comprising the variable regions of the heavy ($V_H$) and light ($V_L$) domains of an antibody, connected with a short linker peptide comprising about 10-25 amino acids. Typically, the linker peptide is rich in glycine to confer flexibility and rich in serine or threonine to increase solubility. ScFvs retain the specificity of the original full-length antibody, despite removal the constant regions (Fc regions) and introduction of the linker sequence. In embodiments, the $V_H$ domain is upstream of the $V_L$ domain; in other embodiments, the $V_L$ domain is upstream of the $V_H$ domain.

In embodiments, provided herein is a single-chain variable fragment (ScFv) derived from anti-c-Met monoclonal antibody MetMAb, wherein the ScFv specifically binds to MET receptor. MetMAb is also known as onartuzumab, a humanized anti-c-MET antibody developed by Genentech, Inc. (San Francisco, CA). MetMAb is described in US 2011/0262436, which is hereby incorporated by reference in its entirety. In embodiments, the ScFv comprises a signal peptide, a $V_H$ domain of MetMAb, a linker peptide, and a $V_L$ domain of MetMAb.

Figure 1B:
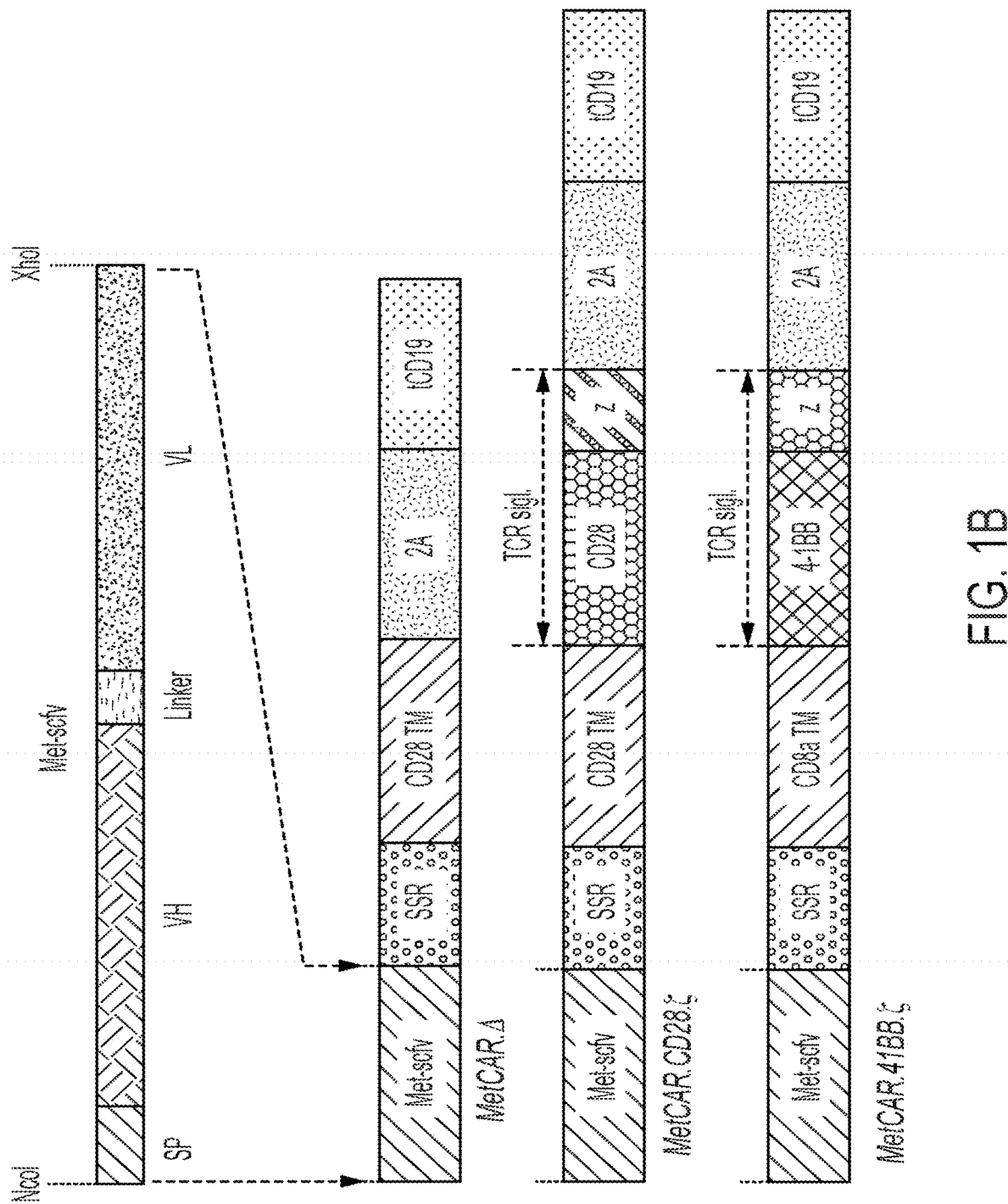
FIG. 1B is a schematic representation of MetCAR structures. The synthesized Met-ScFv sequence comprises a signaling peptide domain (SP) followed by the $V_H$ and $V_L$ domains of Met mAb connected by a common linker. The Met-ScFv sequence was cloned into a mock vector (CARA) and two 2nd generation CAR vectors (CAR.CD28.ζ. and CAR.4-1BB.ζ.) under unique NcoI-XhoI restriction sites. A CD19 tag is designed in the vector for easy determination of T cell transduction efficacy and isolation.

A schematic diagram of an ScFv according to the present disclosure is set forth in FIG. 1B. In embodiments, the $V_H$ domain shares at least 80%, at least 85%, at least 90%, at least 95%, at least 96%, at least 97%, at least 98%, at least 99%, or 100% identity with SEQ ID NO: 4 or SEQ ID NO: 8. In a specific embodiment, the $V_H$ domain comprises SEQ ID NO: 4, having the sequence:

```
                                       (SEQ ID NO: 4)
GAGGTGCAGCTGGTGGAGTCTGGTGGCGGCCTGGTTCAGCCAGG

CGGTAGCCTGCGTCTGTCTTGCGCAGCCAGCGGCTACACCTTCA

CCAGCTATTGGCTGCACTGGGTGCGCCAAGCCCCAGGCAAGGGT

CTGGAGTGGGTGGGTATGATTGACCCTAGCAACAGCGACACCCG

TTTCAATCCAAACTTCAAAGACCGCTTTACCATTAGCGCCGACA

CCAGCAAGAACACCGCCTATCTGCAGATGAACTCTCTCCGCGCC

GAGGACACCGCCGTGTACTACTGCGCCACCTATCGCAGCTACGT

TACACCTCTGGACTACTGGGGCCAGGGCACCCTGGTGACCGTGA

GCAGC.
```

In a specific embodiment, the $V_H$ domain comprises SEQ ID NO: 8, having the sequence:

(SEQ ID NO: 8)
EVQLVESGGGLVQPGGSLRLSCAASGYTFTSYWLHWVRQAPGKG

LEWVGMIDPSNSDTRFNPNFKDRFTISADTSKNTAYLQMNSLRA

EDTAVYYCATYRSYVTPLDYWGQGTLVTVSS.

In embodiments, the V$_L$ domain shares at least 80%, at least 85%, at least 90%, at least 95%, at least 96%, at least 97%, at least 98%, at least 99%, or 100% identity with SEQ ID NO: 5 or SEQ ID NO: 9. In a specific embodiment, the V$_L$ domain comprises SEQ ID NO: 5, having the sequence:

(SEQ ID NO: 5)
GACATTCAGATGACACAGTCTCCTAGCTCTCTGTCTGCCTCTGT

GGGCGACCGTGTTACCATTACCTGCAAAAGCAGCCAGAGCCTGC

TGTACACCAGCAGCCAGAAGAACTATCTGGCATGGTATCAGCAG

AAGCCAGGCAAAGCACCTAAACTGCTCATCTACTGGGCCAGCAC

CCGCGAAAGCGGCGTTCCTTCTCGCTTTAGCGGCAGCGGTAGCG

GTACAGACTTCACCCTGACCATCAGCAGCCTGCAGCCTGAGGAT

TTCGCCACCTATTACTGCCAGCAGTACTACGCCTATCCTTGGAC

ATTCGGTCAGGGCACAAAAGTGGAGATCAAGGAT, wherein the sequence is mutated with respect to MetMAb at the underlined portion to avoid an internal NcoI restriction site.

In a specific embodiment, the V$_L$ domain comprises SEQ ID NO: 9, having the sequence:

(SEQ ID NO: 9)
DIQMTQSPSSLSASVGDRVTITCKSSQSLLYTSSQKNYLAWYQQ

KPGKAPKLLIYWASTRESGVPSRFSGSGSGTDFTLTISSLQPED

FATYYCQQYYAYPWTFGQGTKVEIKD.

The skilled artisan will appreciate that various linker sequences are suitable for use in the disclosed ScFvs. In embodiments, the linker sequence disposed between the V$_H$ and V$_L$ sequences shares 80%, at least 85%, at least 90%, at least 95%, at least 96%, at least 97%, at least 98%, at least 99%, or 100% identity with SEQ ID NO: 3. In a specific embodiment, the linker sequence comprises SEQ ID NO: 3, having the sequence:

(SEQ ID NO: 3)
GGAGGCGGAGGATCAGGCGGCGGAGGAAGTGGCGGAGGGGGAAG

C.

In embodiments, the ScFv comprises a signaling peptide sequence (SP) upstream of the variable domains. In embodiments, the SP sequence shares at least 80%, at least 85%, at least 90%, at least 95%, at least 96%, at least 97%, at least 98%, at least 99%, or 100% identity with SEQ ID NO: 2. In a specific embodiment, the SP sequence comprises SEQ ID NO: 2, having the sequence:

(SEQ ID NO: 2)
ATTGGATCTGGCGCATCCTGTTTCTCGTGGGAGCCGCCACAGGC

GCCCACTCT.

In another embodiment, the ScFv shares at least 80%, at least 85%, at least 90%, at least 95%, at least 96%, at least 97%, at least 98%, at least 99%, or at least 100% identity with SEQ ID NO: 1 or SEQ ID NO: 7. In a specific embodiment, the ScFv comprises SEQ ID NO: 1, having the sequence:

(SEQ ID NO: 1)
ATTGGATCTGGCGCATCCTGTTTCTCGTGGGAGCCGCCACAGGC

GCCCACTCTGAGGTGCAGCTGGTGGAGTCTGGTGGCGGCCTGGT

TCAGCCAGGCGGTAGCCTGCGTCTGTCTTGCGCAGCCAGCGGCT

ACACCTTCACCAGCTATTGGCTGCACTGGGTGCGCCAAGCCCCA

GGCAAGGGTCTGGAGTGGGTGGGTATGATTGACCCTAGCAACAG

CGACACCCGTTTCAATCCAAACTTCAAAGACCGCTTTACCATTA

GCGCCGACACCAGCAAGAACACCGCCTATCTGCAGATGAACTCT

CTCCGCGCCGAGGACACCGCCGTGTACTACTGCGCCACCTATCG

CAGCTACGTTACACCTCTGGACTACTGGGGCCAGGGCACCCTGG

TGACCGTGAGCAGCGGAGGCGGAGGATCAGGCGGCGGAGGAAGT

GGCGGAGGGGGAAGCGACATTCAGATGACACAGTCTCCTAGCTC

TCTGTCTGCCTCTGTGGGCGACCGTGTTACCATTACCTGCAAAA

GCAGCCAGAGCCTGCTGTACACCAGCAGCCAGAAGAACTATCTG

GCATGGTATCAGCAGAAGCCAGGCAAAGCACCTAAACTGCTCAT

CTACTGGGCCAGCACCCGCGAAAGCGGCGTTCCTTCTCGCTTTA

GCGGCAGCGGTAGCGGTACAGACTTCACCCTGACCATCAGCAGC

CTGCAGCCTGAGGATTTCGCCACCTATTACTGCCAGCAGTACTA

CGCCTATCCTTGGACATTCGGTCAGGGCACAAAAGTGGAGATCA

AGGAT.

In another specific embodiment, the ScFv comprises SEQ ID NO: 7, having the sequence:

(SEQ ID NO: 7)
MDWIWRILFLVGAATGAHSEVQLVESGGGLVQPGGSLRLSCAAS

GYTFTSYWLHWVRQAPGKGLEWVGMIDPSNSDTRFNPNFKDRFT

ISADTSKNTAYLQMNSLRAEDTAVYYCATYRSYVTPLDYWGQGT

LVTVSSGGGGSGGGGSGGGGSDIQMTQSPSSLSASVGDRVTITC

KSSQSLLYTSSQKNYLAWYQQKPGKAPKWYWASTRESGVPSRFS

GSGSGTDFTLTISSLQPEDFATYYCQQYYAYPWTFGQGTKVEIK

DLE.

In a specific embodiment, the V$_H$ and/or V$_L$ domain of MetMAb is modified to remove internal restriction sites to facilitate cloning.

Optionally, the ScFv comprises restriction sites at the 3' and 5' ends to facilitate cloning into a suitable vector. The skilled artisan will appreciate that various restriction sites are suitable for use and may be selected to correspond with the vector of choice and compatibility for ligation. In certain embodiments, the restrictions sites are selected from NcoI, XhoI, EcoRI, NotI, HindIII, BamHI, and the like. In a specific embodiment, the ScFv construct comprises a NcoI restriction site at the 5' end and an XhoI restriction site at the 3' end. In embodiments, the ScFv construct comprising restriction sites shares at least 80%, at least 85%, at least 90%, at least 95%, at least 96%, at least 97%, at least 98%, at least 99%, or at least 100% identity with SEQ ID NO: 6. In a specific embodiment, the ScFv comprising restriction sites comprises SEQ ID NO: 6, having the sequence:

```
                                        (SEQ ID NO: 6)
CCATGGATTGGATCTGGCGCATCCTGTTTCTCGTGGGAGCCGCC

ACAGGCGCCCACTCTGAGGTGCAGCTGGTGGAGTCTGGTGGCGG

CCTGGTTCAGCCAGGCGGTAGCCTGCGTCTGTCTTGCGCAGCCA

GCGGCTACACCTTCACCAGCTATTGGCTGCACTGGGTGCGCCAA

GCCCCAGGCAAGGGTCTGGAGTGGGTGGGTATGATTGACCCTAG

CAACAGCGACACCCGTTTCAATCCAAACTTCAAAGACCGCTTTA

CCATTAGCGCCGACACCAGCAAGAACACCGCCTATCTGCAGATG

AACTCTCTCCGCGCCGAGGACACCGCCGTGTACTACTGCGCCAC

CTATCGCAGCTACGTTACACCTCTGGACTACTGGGGCCAGGGCA

CCCTGGTGACCGTGAGCAGCGGAGGCGGAGGATCAGGCGGCGGA

GGAAGTGGCGGAGGGGAAGCGACATTCAGATGACACAGTCTCC

TAGCTCTCTGTCTGCCTCTGTGGGCGACCGTGTTACCATTACCT

GCAAAAGCAGCCAGAGCCTGCTGTACACCAGCAGCCAGAAGAAC

TATCTGGCATGGTATCAGCAGAAGCCAGGCAAAGCACCTAAACT

GCTCATCTACTGGGCCAGCACCCGCGAAAGCGGCGTTCCTTCTC

GCTTTAGCGGCAGCGGTAGCGGTACAGACTTCACCCTGACCATC

AGCAGCCTGCAGCCTGAGGATTTCGCCACCTATTACTGCCAGCA

GTACTACGCCTATCCTTGGACATTCGGTCAGGGCACAAAAGTGG

AGATCAAGGATCTCGAG.
```

In embodiments, the ScFv comprises or consists of SEQ ID NO: 1 or SEQ ID NO: 7. In other embodiments, the ScFv construct comprises SEQ ID NO: 2, SEQ ID NO: 3, SEQ ID NO: 4, and SEQ ID NO: 5. In other embodiments, the ScFv construct comprises SEQ ID NO: 6.

In another embodiment, a single-chain variable fragment fusion protein is provided. In a specific embodiment, the fusion protein comprises SEQ ID NO: 7. In another embodiment, the fusion protein shares at least 80%, at least 85%, at least 90%, at least 95%, at least 96%, at least 97%, at least 98%, at least 99%, or 100% identity with SEQ ID NO: 7.

The skilled artisan will appreciate that modified sequences sharing sufficient identity with the disclosed sequences will also be functional in the disclosed constructs and peptides. Accordingly, in embodiments, the sequences described herein share at least 80%, at least 85%, at least 90%, at least 95%, at least 96%, at least 97%, at least 98%, at least 99%, or 100% identity with the corresponding SEQ IDs.

Chimeric Antigen Receptor (CAR) Vectors

The term "chimeric antigen receptor" or CAR as used herein refers to a cell-surface receptor comprising an extracellular ligand binding domain, a transmembrane domain (TM), and a cytoplasmic co-stimulatory signaling domain in a combination that is not naturally found together on a single protein. This particularly includes receptors wherein the extracellular domain and the cytoplasmic domain are not naturally found together on a single receptor protein. Further, the chimeric receptor is different from the TCR expressed in the native T cell lymphocyte.

Provided is an expression vector comprising an ScFv as described herein. In embodiments, the expression vector is a chimeric antigen receptor (CAR) vector. The skilled artisan will appreciate that various CAR vectors are suitable for use with the disclosed ScFvs. Suitable CAR vectors include, but are not limited to, viral CAR vectors. Such viral vectors may include retroviral vectors, lentiviral vectors, adenoviral vectors, or adeno-associated viral vectors. Viral vectors may include first, second, third, or fourth generation gammaretrovirus or lentiviral vectors, such as those disclosed in Zhang, et al., *Engineering CAR-T cells, Biomarker Research* 5(22): 1-6 (2017). In a specific embodiment, the CAR vector is a second generation CAR vector selected from the group consisting of CAR.4-1BB.ζ. and CAR.CD28.ζ.

A schematic diagram of illustrative CAR vectors according to an embodiment of the disclosure is set forth in FIG. 1B. In embodiments, the CAR vector is a second generation CAR vector comprising a short non-signaling spacer domain (SSR) disposed between the ScFv and a T cell receptor (TCR) transmembrane domain (TM). In embodiments, the TM domain may comprise a CD28 TM domain or a CD8a TM domain, or other suitable transmembrane domain as desired. The skilled artisan will appreciate that the TM domain may be selected or altered, as desired, to optimize the binding affinity of the construct to the MET extracellular domain.

The second generation CAR vectors described herein comprise an intracellular TCR co-stimulatory signaling module (TCR sigl.) for promoting activation of T cells and avoiding apoptosis. In embodiments, the TCR signaling module comprises a CD28 or 4-1BB domain and a zeta (z) domain. In embodiments, the CAR vectors disclosed herein further comprise a 2A self-cleaving peptide region and a CD19 tag for evaluating T cell transfection efficacy and MetCAR-T cell purification.

In a specific embodiment, the MetCAR vector is selected from the group consisting of MetCAR.4-1BB.ζ. and MetCAR.CD28.ζ.

CART Cells

Genetic modification for introduction of the CAR construct into T cells can be accomplished by transducing (or otherwise delivering) a T cell with a recombinant DNA or RNA construct, such as for example, a vector. A vector may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

"CAR T cells" refer to a T cell or population thereof, which has been modified through molecular biological methods to express a chimeric antigen receptor (CAR) on the T cell surface. The CAR is a polypeptide having a pre-defined binding specificity to a desired target expressed operably connected to (e.g., as a fusion, separate chains linked by one or more disulfide bonds, etc.) the intracellular part of a T-cell activation domain. By bypassing MHC class I and class II restriction, CAR engineered T cells of both CD8+ and CD4+ subsets can be recruited for redirected target cell recognition. The most common CARs are fusions of immunoglobulin binding functionality (e.g., as a single-chain variable fragment (ScFv) derived from a monoclonal antibody) to CD3-zeta (CD3) transmembrane and endodomain. Such molecules result in the transmission of a zeta signal in response to recognition by the immunoglobulin binding functionality of its target. There are, however, many alternatives. By way of example, an antigen recognition domain from native T-cell receptor (TCR) alpha and beta single chains may be used as the binding functionality. Alternatively, receptor ectodomains (e.g. CD4 ectodomain) or cytokines (which leads to recognition of cells bearing the cognate cytokine receptor) may be employed. In embodiments, T cells suitable for use include autologous or allogeneic T cells.

Provided herein is a human T cell transduced with a MetCAR vector according to embodiments of the present disclosure. In embodiments, the vector comprises an ScFv construct according to the present disclosure. In embodiments, the T cell is a human T cell transduced with a chimeric antigen receptor (CAR) viral vector comprising a single-chain variable fragment (ScFv) derived from MetMAb, wherein the ScFv specifically binds MET receptor. In a specific embodiment, the human T cell is transduced with a vector selected from the group consisting of Met-CAR.4-1BB.ζ. and MetCAR.CD28.ζ.

Methods of Treatment

In embodiments, a method of treating a cancer characterized by overexpression of MET in a subject in need thereof is provided, the method comprising administering to the subject an effective amount of human T cells transduced with a CAR vector comprising an ScFv construct derived from MetMAb, as disclosed herein.

In embodiments, the cancer characterized by overexpression of MET is selected from the group consisting of liver cancer (including hepatocellular carcinoma (HCC)), lung cancer (including small cell lung cancer and non-small cell lung cancer), malignant mesothelioma, ovarian cancer, colon cancer, breast cancer, pancreatic cancer, prostate cancer, gastric carcinomas, and glioblastoma. In a specific embodiment, the cancer characterized by overexpression of MET is hepatocellular carcinoma (HCC).

Optionally, the method further comprises administering to the subject an effective amount of one or more additional therapeutic agents. In a specific embodiment, the one or more additional therapeutic agents are selected from the group consisting of chemotherapeutic agents, radiation therapy, and combinations thereof.

In a specific embodiment, the cancer to be treated is HCC and the additional therapeutic agents are selected from the group consisting of sorafenib, cabozantinib, tivantinib, and combinations thereof. Optionally, the method further comprises administering radiation therapy to the subject.

In another embodiment, a method of treating a MET-positive cancer in a subject in need thereof is provided, the method comprising administering to the subject an effective amount of human T cells transduced with a CAR vector comprising an ScFv construct derived from MetMAb, as disclosed herein.

As used herein, the term "MET-positive cancer" refers to a cancer comprising cells, illustratively tumor cells, that express MET at a higher expression level compared to surrounding normal cells.

In embodiments, the MET-positive cancer is selected from the group consisting of liver cancer (including hepatocellular carcinoma (HCC)), lung cancer (including small cell lung cancer and non-small cell lung cancer), malignant mesothelioma, ovarian cancer, colon cancer, breast cancer, pancreatic cancer, prostate cancer, gastric carcinomas, and glioblastoma. In a specific embodiment, the MET-positive cancer is hepatocellular carcinoma (HCC).

Optionally, the method further comprises administering to the subject an effective amount of one or more additional therapeutic agents. In a specific embodiment, the one or more additional therapeutic agents are selected from the group consisting of chemotherapeutic agents, radiation therapy, and combinations thereof.

In a specific embodiment, the cancer to be treated is HCC and the additional therapeutic agents are selected from the group consisting of sorafenib, cabozantinib, tivantinib, and combinations thereof. Optionally, the method further comprises administering radiation therapy to the subject.

The cell compositions described herein can be administered to a host, either alone or in combination with a pharmaceutically acceptable excipient, in an amount sufficient to induce an appropriate anti-tumor response. The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

Effective amounts of CAR T cells can be determined by a physician with consideration of individual differences in age, weight, tumor size, extent of infection or metastasis, and condition of the patient (subject). It can generally be stated that a pharmaceutical composition comprising the CAR T cells described herein may be administered at a dosage of 100 to 1000 cells/kg body weight, including all integer values within those ranges. T cell compositions may also be administered multiple times at these dosages. The cells can be administered by using infusion techniques that are commonly known in immunotherapy. The optimal dosage and treatment regime for a particular patient can readily be determined by one skilled in the art by monitoring the patient for signs of disease and adjusting the treatment accordingly.

An effective amount of the cell compositions described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the cell compositions. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The disclosed methods are not limited to dosing intervals that are spaced equally in time, but encompass doses at non-equal intervals, such as a priming schedule consisting of administration, illustratively, at 1 day, 4 days, 7 days, and 25 days.

An effective amount for a particular subject may vary depending on factors such as the condition being treated, the overall health of the patient, the route and dose of administration and the severity of side effects. Determination of the effective amount is within the purview of the ordinary skilled artisan.

The cell compositions of the present invention can be administered in a dose, or dosages, where each dose comprises at least 100 cells/kg body weight or more; at least 1000 cells/kg body weight or more; at least 10,000 cells; at least 100,000 cells; at least 1 million cells; at least 10 million cells; at least 100 million cells; at least 1 billion cells; at least 10 billion cells; or at least 100 billion cells/kg body weight.

A dosing schedule of, for example, once/week, twice/week, three times/week, four times/week, five times/week, six times/week, seven times/week, once every two weeks, once every three weeks, once every four weeks, once every five weeks, and the like, is contemplated herein. The dosing schedules encompass dosing for a total period of time comprising, for example, one week, two weeks, three weeks, four weeks, five weeks, six weeks, two months, three months, four months, five months, six months, seven months, eight months, nine months, ten months, eleven months, or twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Optionally, one or more additional therapeutic agent is co-administered to the subject. As used herein, co-administration need not refer to administration at the same time in an individual, but rather may include administrations that are spaced by hours or even days, weeks, or longer, as long as the administration of multiple therapeutic agents is the result of a single treatment plan.

Pharmaceutical Compositions

In another embodiment, a pharmaceutical composition is provided, the composition comprising: a human T cell transduced with a chimeric antigen receptor (CAR) vector comprising a single-chain variable fragment (ScFv) derived from MetMAb, wherein the ScFv specifically binds to MET receptor; and a pharmaceutically-acceptable carrier.

A "pharmaceutically-acceptable carrier" includes, but is not limited to, sterile distilled water, saline, phosphate buffered solutions, amino acid based buffers, or bicarbonate buffered solutions. A carrier selected and the amount of carrier used will depend upon the mode of administration. Administration comprises an injection, infusion, or a combination thereof. In a specific embodiment, administration comprises infusion of the pharmaceutical composition comprising CAR T cells transduced with a MetCAR vector according to embodiments of the present disclosure.

EXAMPLES

The following examples are given by way of illustration and are in no way intended to limit the scope of the present disclosure.

Example 1. Materials and Methods

Cell Lines

Human HCC cells C3A and SNU398 were obtained from American Tissue Type Collection (ATCC); JHH5 was obtained from the Japanese Collection of Research Bioresources (JCRB). MHCC97H was provided by Fudan University Liver Cancer Institute. Briefly, the SNU398 cell line was grown in RPMI-1640 supplemented with 10% FBS. MHCC97H and C3A were grown in DMEM with 10% FBS. JHH5 was grown in Williams E with 10% FBS.

Generation of Retroviral Based Specific Met-Targeting CARs

The MET-specific single chain variable domain (Met-scfv) was synthesized based on a published MET monoclonal antibody MetMAb (US 2011/0262436), to contain the immunoglobulin signaling peptide and the variable heavy chain ($V_H$) and light chain ($V_L$) according to the MetMAb antibody sequence (see Merchant, et al., *Monovalent antibody design and mechanism of action of onartuzumab, a MET antagonist with anti-tumor activity as a therapeutic agent*, Proc. Natl. Acad. Sci. USA 110(32): E2987-96 (2013)). The construct was further cloned into pUC5 as a transport vector using the NcoI-XhoI (5'-3') sites. The Met-scfv was further subcloned into 2 secondary CAR vectors (CAR.SSR.CD28.ζ, and CAR.SSR.4-1BB.ζ) and an empty CAR.SSR.Δ vector without a TCR endodomain. All cloning of MetCARs was verified by sequencing (GeneWiz). RD114-pseudotyped retroviral particles were generated by transient transfection of 293T cells.

Generation of CAR T Cells

Human whole blood was obtained from healthy donors. To generate MetCAR T cells, peripheral blood mononuclear cells (PBMCs) were isolated by ficole (GE Healthcare Bio-Science AB, Uppsala, Sweden) gradient centrifugation followed by stimulation on non-tissue culture 24-well plates pre-coated with CD3 and CD28 antibodies (Miltenyi Biotec Inc) for 24 h. On day 2, recombinant human interleukin-7 and interleukin-15 (IL-7 at 10 ng/ml; and IL-15 at 5 ng/ml; Miltenyi Biotech Bergisch Gladbach, Germany) were added into cultures. On day 3, CD3/CD28-stimulated T cells ($2.5 \times 10^5$ cells/well) were transduced on RetroNectin (TaKaRa Bio Inc.) coated plates in the presence of IL-7 and IL-15. On day 5, T cells were transferred into new wells and subsequently expanded with IL-7 and IL-15. Nontransduced (NT) T cells were activated with CD3/CD28 and expanded in parallel with IL-7 and IL-15. Expression of MetCARs was determined 4 to 5 days post-transduction using flow cytometry.

Flow Cytometry

Cells were collected and washed with PBS containing 1% FBS and incubated with antibodies for 30 minutes, followed by analysis using a flow cytometer (FACSCalibur, BD). Data analysis was performed using FlowJo software (FlowJo, LLC Ashland, OR). Antibodies and isotype controls used are CD3 FITC, CD19 PE, IgG1 FITC, and IgG1 PE (Invitrogen, San Diego, CA).

MetCAR-T Cell Mediated Cytotoxicity Against HCC Cells and Cytokine Release In Vitro To test MetCAR T cell-mediated cytotoxicity, HCC cells were seeded in 96-well plates at $2 \times 10^4$ cells/well) and grown at 37° C. for 24 hrs, followed by adding nontransduced (NT) and MetCAR transduced healthy T cells into each well at 10:1, 5:1, 2.5:1, and 1.25:1 (Effector T cell:Tumor cell, E:T) ratios for co-culture. After an additional 24 hrs, effector T cells were carefully washed out. The viability of tumor cells was determined using MTS assay (Promega). To determine cytokine release, HCC cells were seeded in 24-well plates at $5\times10^5$ cells/well and grown overnight, followed by co-culture with MetCAR transduced T cells at E:T=2:1 ratio for an additional 24 hrs. The conditioned medium is collected from each well to determine IL-2 and IFNγ concentrations using ELISA (R&D, Minneapolis, MN).

Western Blot

To test MetCAR mediated T cell activation, MetCAR T cells were harvested 72 hrs after MetCAR transduction and lysed in RIPA buffer (Thermo Fisher Scientific, Rockford, IL) containing protease inhibitors (Thermo Fisher Scientific, Rockford, IL). To test Met signaling activation in HCC cells, MHCC97H, JHH5, C3A, and SNU398 cells were cultured in 10-cm dishes until 80% confluence followed by cell lysis. Protein concentration was determined using the DC protein assay kit (Bio-Rad, Hercules, CA). Equal amounts of total protein were run on 10% SDS-PAGE gels (Life Technologies, Carlsbad, CA) and transferred to polyvinylidene difluoride (PVDF) membranes (Life Technologies, Carlsbad, CA). Antibody-protein complexes were detected using SuperSignal West Dura Extended Duration Substrate (Thermo Fisher Scientific, Rockford, IL). Images were taken using ChemiDoc (Bio-Rad, Hercules, CA). Antibodies against human Met (clone 25H2), phospho-Met (Y1234/1235), AKT, phospho-AKT (S473), p42/44 MAPK, phospho-p42/44 MAPK (T202/Y204), (all from Cell Signaling Technology, Danvers, MA), anti-CD3ζ (sc-1239), anti-phospho-CD3.ζ (sc-9975), (from Santa Cruz Biotechnology, CA), and β-actin (clone AC-15, Abcam) were used. Secondary antibodies used were goat anti-rabbit IgG-HRP and goat anti-mouse IgG-HRP (Santa Cruz Biotechnology).

Confocal Microscopic Real Time Imaging

To visualize MetCAR T cell mediated killing activity, MHCC97H$^{mCherry}$ cells were seeded in 35 mm dishes with glass bottom at $5\times10^5$ cells/well and grown at 37° C. for 24 hrs for co-culture with MetCAR T cells generated as described above. Prior to co-culture, MetCAR T cells were stained with a mitochondrial fluorescence dye (Mitotraker Green FM, Thermofisher) at 300 nM for 30 min, washed with PBS, and resuspended with culture medium, followed by co-culture with MHCC97H$^{mCherry}$ cells at 10:1 E:T ratios for additional 24 hrs under a confocal microscope (Letica TCS SP8). For real time imaging, cells were maintained at normal culture condition (37° C. with 5% $CO_2$) and images were taken automatically every 5-10 min. At each time point, images were sequentially acquired under mCherry (ex/em=552/589-660). MitoTracker Green (ex/em=488/497-549) and Differential interference contrast (DIC) channels. After all images were acquired, LAS X software (Leica Microsystems Inc.) was used to produce a video clip for each experiment (data not shown).

Statistical Analysis

GraphPad Prism 5 software (GraphPad software, La Jolla, CA) was used for statistical analysis. To determine the effectiveness of MetCAR T cells in vitro, the average cell survival rate, IL-2 and IFNγ release of each group were analyzed with Student's t test ($p<0.05$).

Example 2. Generation of MetCAR Constructs

MetMAb (onartuzumab) is a humanized monoclonal antibody developed for MET-targeting therapy against cancer, but which failed in Phase III clinical trials due to a lack of efficacy. While clinical trial results were disappointing, the present disclosure demonstrates that its specific MET binding domain can be modified for MET-targeting using CAR T cell therapy as an alternative strategy. While not desiring to be bound by theory, it is believed that because MetCAR T cells function through TCR activation rather than MET RTK inhibition, efficacy is not dependent on HGF/MET pathway activity, does not lead to RTK signaling bypass, and therefore may inhibit MET-positive tumors more effectively than MetMAb or other specific MET TKIs.

Figure 1C:
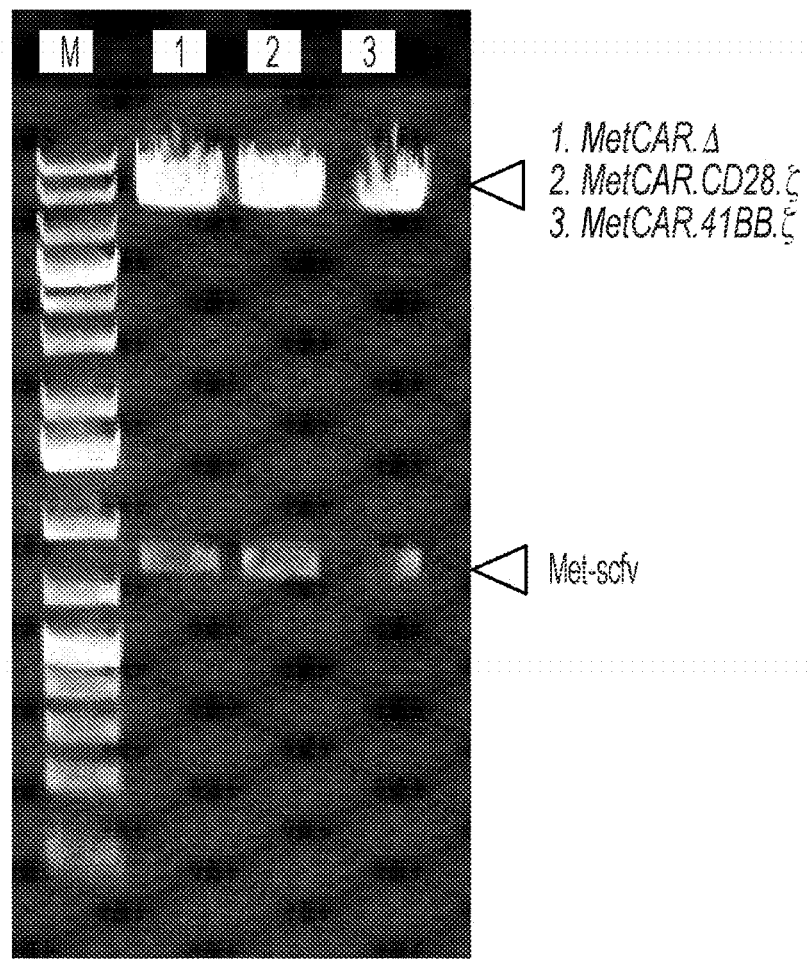
FIG. 1C is an image showing MetCARs validation determined using NcoI-XhoI digestion showing the inserted Met-ScFv fragments (Lanes 1-3, lower band, 801 bp).

To generate ScFv from MetMab, the published crystal structure of the Fab fragment of MetMAb antibody (FIG. 1A, light chain, light grey and heavy chain, dark grey) binding to MET Sema-PSI domain was analyzed. The sequences of variable heavy chain ($V_H$) and variable light chain ($V_L$) domains were confirmed as the minimum requirements for binding with the MET extracellular domain (FIG. 1A, circled). Based on this result, the Met-ScFv domain was synthesized (FIG. 1B top panel) and constructed into two retroviral based second-generation CAR vectors (FIG. 1B, CAR.CD28.ζ. and CAR.4-1BB.ζ.). In both cases, there is a short non-signaling spacer domain (SSR) disposed between the Met-ScFv and a TCR transmembrane (TM) domain (CD28 TM or CD8a TM), which can be adjusted further to improve the binding affinity to MET extracellular domain. Both vectors comprise a TCR signaling module (TCR sigl.) and a CD19 tag that can be used to determine T cell transfection efficacy and MetCAR-T cell purification. An empty CAR vector with Met-Scfv but lacking TCR sigl. domain is also constructed for negative control (FIG. 1B, MetCARΔ). For all MetCAR constructs, the inserted Met-scfv fragment has been validated by size (FIG. 1C, lower band, 801 bp), followed by Sanger Sequencing to eliminate unexpected mutations.

Example 3. MetCAR T Cell Production and Characterization

Figure 2C:
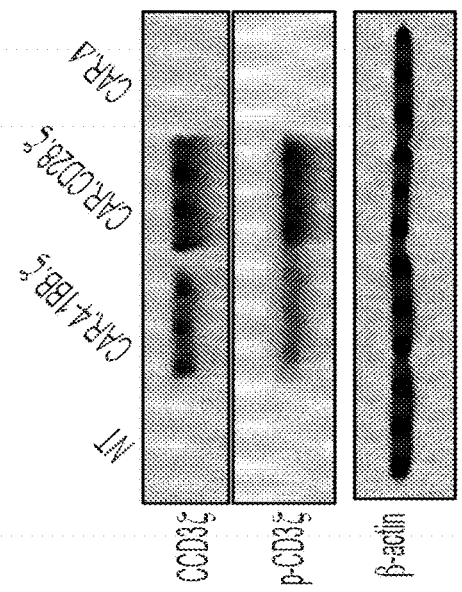
FIG. 2C is an image of a Western blot showing MetCAR expression using CD3ζ as a marker.
Figure 2B:
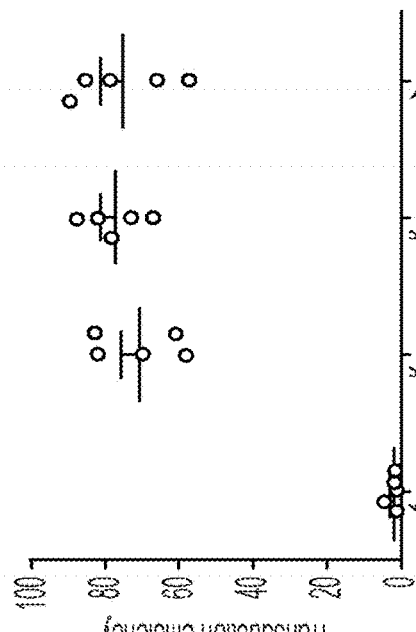
FIG. 2B is a graph summarizing data of MetCAR expression from FIG. 2A. Each dot represents one donor. MetCAR.CD28.ζ. expression=67%-87.6% (n=5); MetCAR.4-1BB.ζ. expression=58.2%-82.6% (n=5).
Figure 2A:
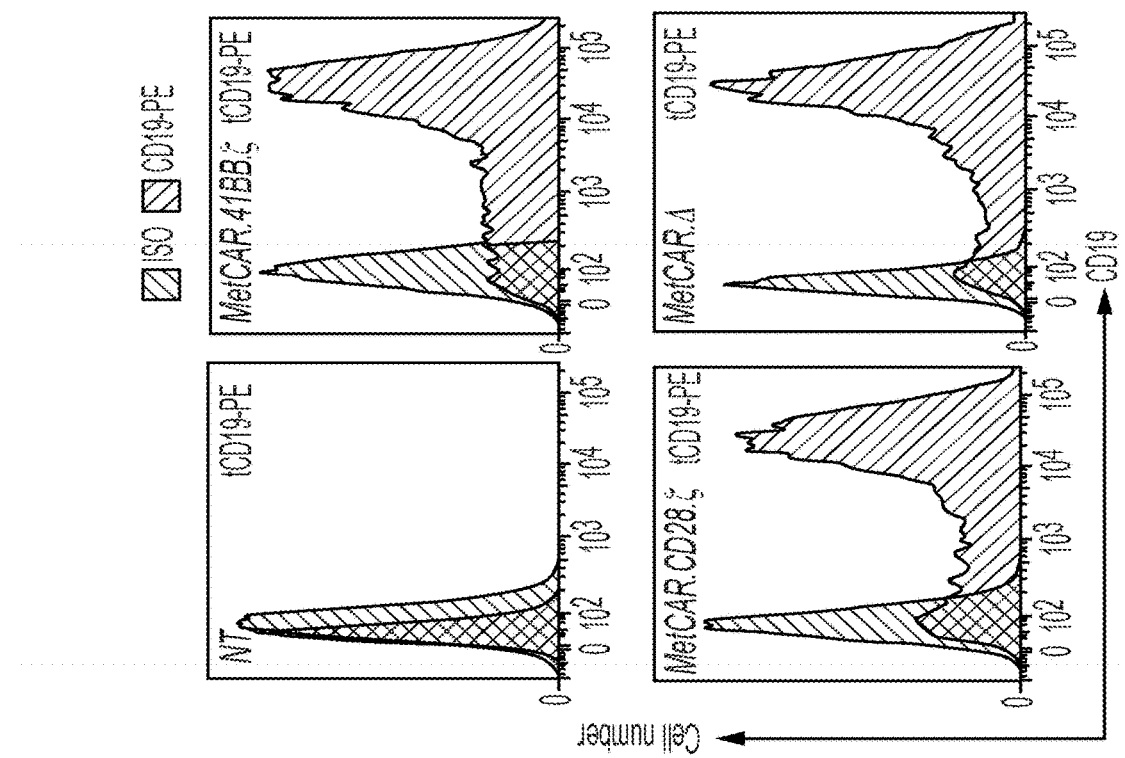
FIG. 2A shows representative MetCAR expression in T cells as examined by flow cytometry using CD19 expression levels. NT=non-transduced T cells.

To produce MetCAR T cells, peripheral blood mononuclear cells (PBMCs) isolated from healthy donors were stimulated with anti-CD3/CD28 antibodies in the presence of IL-7 (10 ng/ml) and IL-15 (5 ng/ml) for 24 hr to expand CD3+ T cells for transduction with MetCARs. CD3+ T cells are regularly tested to reach >90% after stimulation (data not shown). Because all MetCAR constructs use CD19 as a tag, the expression of CD19 by flow cytometer is used as the transduction efficacy (FIGS. 2A, 2B). With NT cells as a negative control, MetCAR transduction efficiency ranged from 60-90% with no significant differences between MetCAR constructs (FIGS. 2A, 2B). MetCAR expression levels were determined using CD3ζ as a marker (FIG. 2C). Results showed that both MetCAR.CD28.ζ. and MetCAR.4-1BB.ζ.-transduced T cells had CD3ζ overexpression comparing with non-transduced or CAR.Δ-transduced T cells. p-CD3ζ expression was also observed in MetCAR.CD28.ζ- and MetCAR.4-1BB.ζ.-transduced T cells (FIG. 2C), indicating the activation of TCR in MetCAR-T cells.

Figure 3A:
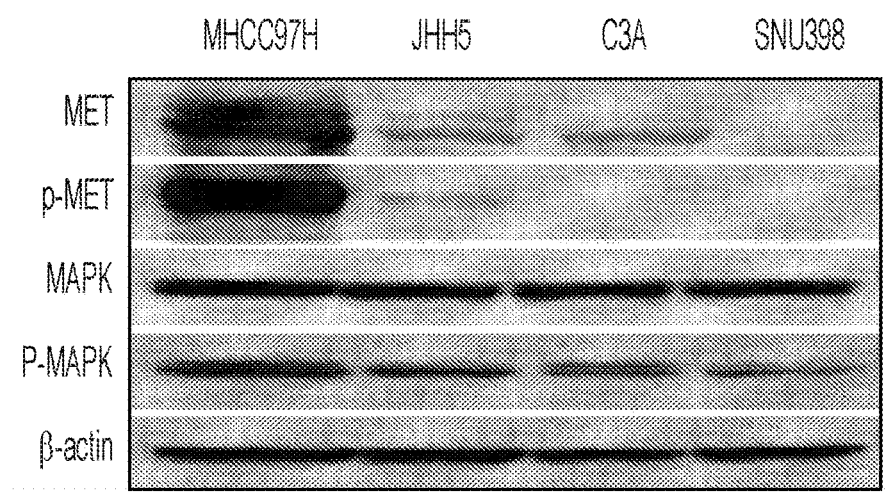
FIG. 3A is an image of a Western blot showing MET/MAPK expression level and pathway activity in MHCC97H, C3A, JHH5, and SNU398 cells. SNU398 cells do not express MET protein.
Figure 3B:
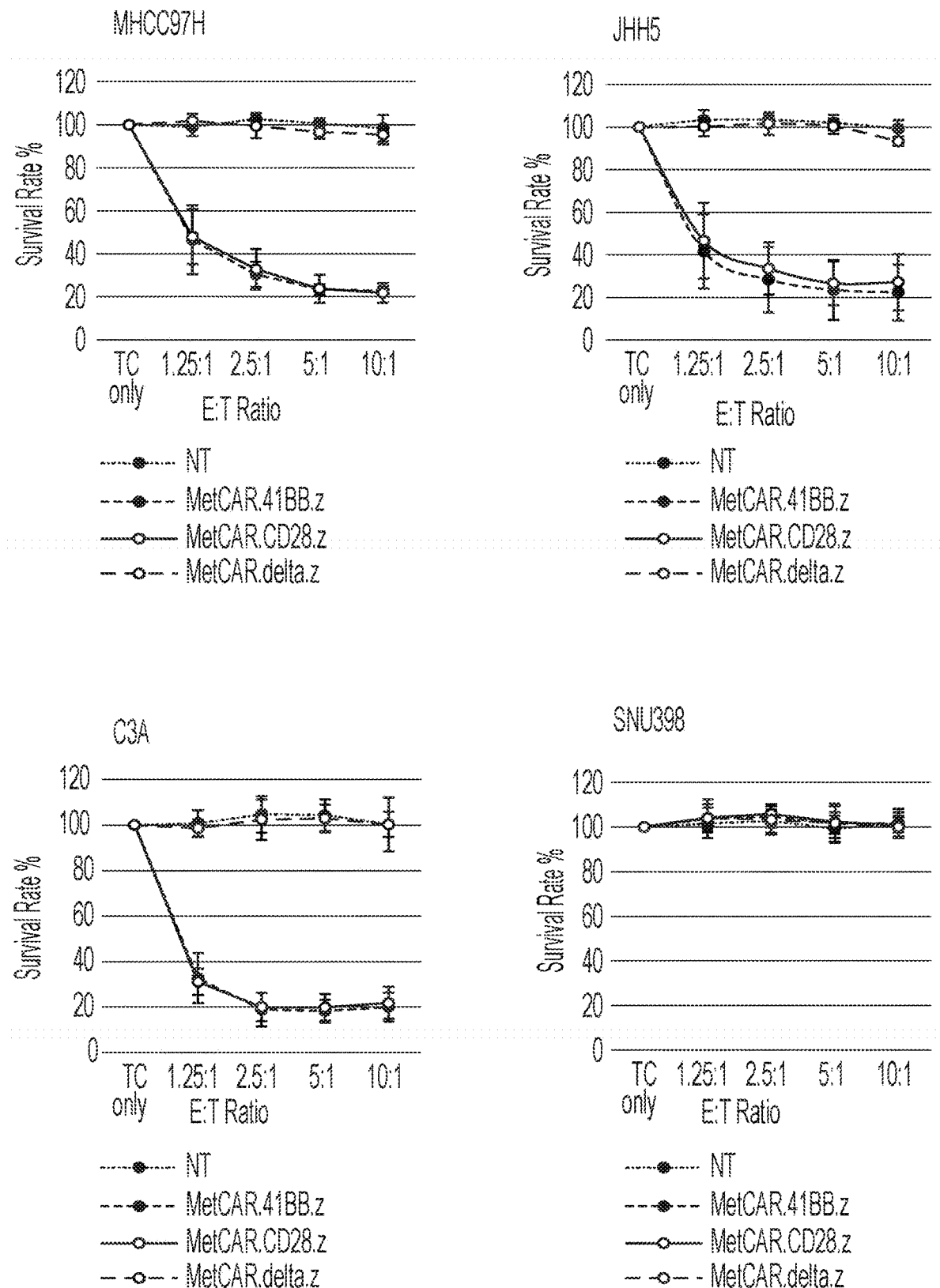
FIG. 3B is a series of graphs showing cytotoxicity of MetCAR T cells against different cell lines at different E:T ratios. MHCC97H, C3A, JHH5, and SNU398 cells were seeded in 96-well plate for 24 hrs followed by adding MetCAR T cells at different E:T ratios. 24 hr cytotoxicity assay as determined by MTS assay. E:T ratio=Effector T cell number:Target tumor cell number. TC=tumor cells only. Survival rate=OD value of treated samples/OD value of TC only samples. Results were averaged from 5 independent experiments with PBMCs from healthy donors (n=5). Triplicates were used for each experiment. Short bar refers to standard deviation. Note that SNU398 showed no response to MetCAR T cells at E:T=10:1 ratio.

Example 4. MetCAR Specifically Target HCC Cells with MET Overexpression In Vitro A panel of HCC cells was previously characterized and showed MET overexpression in MHCC97H, C3A, and JHH5 cells (MET$^{high/+}$), while no expression was detected in SNU398 cells (MET$^{low/-}$), providing good MET-positive and MET-negative samples for testing MetCAR T cell specificity (FIG. 3A). To determine the MET-specific cytotoxicity against HCC cells, MET$^{high+}$ (MHCC97H, C3A, JHH5) and MET$^{low/-}$ (SNU398) HCC cells were co-cultured with NT or MetCAR-T cells at E:T ratio ranging from 1.25:1 to 10:1 (FIG. 3B). Results show that both MetCAR.CD28.ζ and MetCAR.4-1BB.ζ T cells specifically inhibited MHCC97H, C3A, JHH5 cells dose dependently, but had no effect on SNU398 cells (FIG. 3B, p<0.05), demonstrating a high specificity in inhibiting MET positive HCC cells. To confirm the MET-specific cytotoxicity, IL-2 and IFNγ release was assessed in MetCAR-T after co-culture with tumor cells using ELISA analysis. Results showed significantly increased IL-2 (FIG. 4A) and IFNγ (FIG. 4B) release in the conditioned medium from MetCAR.4-1BB.ζ- and MetCAR.CD28.ζ-T cells after co-culture with MHCC97H, C3A, and JHH5 cells but not SNU398 cells. These results indicate that MetCAR.CD28.ζ- and MetCAR.4-1BB.ζ-T cells specifically inhibit MET-positive cells.

Example 5. Real-Time Imaging of MetCAR T Killing Activity Against MHCC97H$^{mCherry}$ Cells In Vitro To visualize the specific recognition and killing activity of Met CAR T cells against MET positive tumor cells, a confocal imaging approach was applied to monitor in real time the dynamic interaction between each of the three MetCAR T cells and MHCC97H$^{mCherry}$ cells during co-culture for continuous 24 hrs. MetCAR cells were shown as green, while MHCC97H$^{mCherry}$ cells were shown as red. At each time point, images were also captured under CID mode to visualize cell morphology in 3D. Results show that MetCAR.4-1BB.ζ-T cells and MetCAR.CD28.ζ-T cells gradually migrated toward MHCC97H$^{mCherry}$ cells, indicating specific recognition. The killing activity commenced after enhanced aggregation of MetCAR T cells with MHCC97H$^{mCherry}$ cells was observed. Results show that MHCC97H$^{mCherry}$ cells became round, shrunk in size, and finally detached from the culture dish, processes indicative of cell death. In contrast, MetCARΔ T cells failed to kill MHCC97H$^{mCherry}$ cells. During the entire period of co-culture, MetCARΔ T cells were floating around the MHCC97H$^{mCherry}$ cells without directed migration or accumulation. Notably, MHCC97H$^{mCherry}$ cells continued to grow well with rapid cell division, with an increase in cell numbers observed at the end of co-culture. Results (captured in video clips, not shown here) indicate that both MetCAR.4-1BB.ζ-T cells and MetCAR.CD28.ζ-T cells specifically recognize and kill MET positive tumor cells in vitro.

Example 6. MetCAR T Cells Release Multi-Panel Cytokines after Co-Culture with MHCC97H Cells Upon activation, CAR T cells release cytokines to re-shape the microenvironment and elicit the cytotoxicity function. To understand the mechanisms of MetCAR T cell killing activity, MHCC97H cells were co-cultured with MetCAR.CD28.ζ. MetCAR.4-1BB.ζ T cells for 24 hrs (E:T=2:1 ratio). Concentrations of 16 cytokines were measured in the co-culture medium, and results were compared using MetCAR.ΔT cells as negative controls (FIGS. 5A-5C).

MHCC97H cells were seeded in 24-well plates for co-culture with MET-CAR T cells at 2:1 (effector T cells:tumor cells) ratio. After 24 hrs, conditioned medium from each well was harvested for multi-panel cytokine release (n=18) test using Human Cytokine Map A platform at Myriad RMB. Each bar represents for the average results from at least 3 healthy donors. Short bar refers to standard deviation. TC refers to tumor cell only. *p<0.05, p<0.01; *p<0.001 as compared with MET-CARA T cells mediated co-culture.

As shown in FIGS. 5A-5C, MetCAR.CD28.ζ, Met-CAR.4-1BB.ζ T cells secreted IL-2 and IFNγ at much higher concentrations than MetCAR.Δ T cells, which is consistent to the ELISA results. In addition, 5 cytokines (MIP-1α, MIP-1β, GM-CSF, TNFβ, and IL-10) were observed to be secreted at significantly higher concentrations in both co-culture mediums from MetCAR.CD28.ζ, or MetCAR.4-1BB.ζ T cells as compared with that from MetCAR.Δ T cells. Although the biological functions of how these cytokines are eliciting the tumor killing activities remains to be elucidated, these results may suggest molecular mechanisms associated with MetCAR-T cell mediated tumor killing activity against HCC.

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

I claim:

1. A chimeric antigen receptor (CAR) vector encoding a single-chain variable fragment (ScFv) derived from an anti-mesenchymal epithelial transition factor (anti-MET) monoclonal antibody, wherein the anti-MET monoclonal antibody is onartuzumab, and wherein the ScFv comprises an amino acid sequence of SEQ ID NO: 7 and specifically binds to MET.

2. The CAR vector according to claim 1, wherein the CAR vector is selected from the group consisting of a MetCAR.4-1BB. ζ vector and a MetCAR. CD28. ζ vector.

3. A human T cell transduced with a chimeric antigen receptor (CAR) vector encoding a single-chain variable fragment (ScFv) derived from an anti-mesenchymal epithelial transition factor (anti-MET) monoclonal antibody, wherein the anti-MET monoclonal antibody is onartuzumab, and wherein the ScFv comprises an amino acid sequence of SEQ ID NO: 7 and specifically binds to MET.

4. The human T cell according to claim 3, wherein the CAR vector is selected from the group consisting of a MetCAR.4-1BB. ζ vector and a MetCAR.CD28. ζ vector.

5. A method of treating a cancer characterized by overexpression of MET in a subject in need thereof, the method comprising administering to the subject an effective amount of a human T cell transduced with a chimeric antigen receptor (CAR) vector encoding comprising a single-chain variable fragment (ScFv) derived from an anti-mesenchymal epithelial transition factor (anti-MET) monoclonal antibody, wherein the anti-MET monoclonal antibody is onartuzumab, and wherein the ScFv comprises an amino acid sequence of SEQ ID NO: 7 and specifically binds to MET.

6. The method according to claim 5, wherein the cancer is a hepatocellular carcinoma (HCC).

7. The method according to claim 5, wherein the CAR vector is selected from the group consisting of a MetCAR.4-1BB. ζ vector and a MetCAR.CD28. ζ vector.

8. The method according to claim 5, further comprising administering to the subject an effective amount of one or more additional therapeutic agents and/or radiation therapy.

9. The method according to claim 8, wherein the one or more additional therapeutic agents are chemotherapeutic agents.

10. A method of treating a MET-positive cancer in a subject in need thereof, the method comprising administering to the subject an effective amount of human T cells according to claim 3.

11. The method according to claim 10, wherein the MET-positive cancer is a hepatocellular carcinoma (HCC).

12. A pharmaceutical composition comprising:
a human T cell transduced with the CAR vector according to claim 1; and
a pharmaceutically-acceptable carrier.

13. The pharmaceutical composition according to claim 12, wherein the CAR vector is selected from the group consisting of a MetCAR.4-1BB. ζ vector and a MetCAR.CD28. ζ vector.

* * * * *